United States Patent
Giannessi et al.

[11] Patent Number: 5,155,102
[45] Date of Patent: Oct. 13, 1992

[54] 1-ALKYL-3-(ACYLAMINO)-ε-CAPROLACTAMES AS ENHANCERS OF LEARNING AND MEMORY AND PHARMACEUTICAL COMPOSITIONS CONTAINING SAME

[75] Inventors: Fabio Giannessi; Orlando Ghirardi; Domenico Misiti; Maria O. Tinti; Roberto Cozzolino, all of Rome; Carlo Scolastico, Milan, all of

[73] Assignee: Sigma-Tau Industrie Farmaceutiche Riunite S.P.A., Rome, Italy

[21] Appl. No.: 718,645

[22] Filed: Jun. 21, 1991

[30] Foreign Application Priority Data

Jun. 21, 1990 [IT] Italy .................. 48087 A/90

[51] Int. Cl.$^5$ .................. A61K 31/55; C07D 223/10; C07D 403/12; C07D 401/14
[52] U.S. Cl. .................. 514/212; 540/529
[58] Field of Search .................. 540/529; 514/212

[56] References Cited
PUBLICATIONS

Chemical Abstracts vol. 26, pp. 3482–3483 (1932) Abstracting Werde "Z. Physiol. Chem." vol. 206 pp. 146–154 (1932).
Ruzicka "Helvetica Chemica Acta", vol. 4, pp. 486–505 (1921).

*Primary Examiner*—Robert T. Bond
*Attorney, Agent, or Firm*—Oblon, Spivak, McClelland, Maier & Neustadt

[57] ABSTRACT

1-alkyl-3-(acylamino)-ε-caprolactames of formula (1)

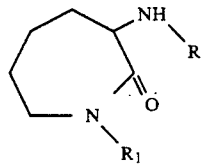

(1)

wherein
R is selected from the group consisting of:
pyrrolidin-2-one-1-acetyl,
p-methoxybenzoyl,
N-benzyloxycarbonyl-(S)-prolyl,
phenylbutanoyl,
3-trifluoromethylbenzoyl,
3,4,5-trimethoxybenzoyl,
nicotinoyl, and
acyl having from 1 to 5 carbon atoms, and
$R_1$ is selected from the group consisting of:
hydrogen,
methoxycarbonylmethyl,
aminocarbonylmethyl,
2-hydroxyethyl, and
formylmethyl,
(provided that, if $R_1$ is hydrogen, R is not formyl or acetyl) are potent enhancers of learning and memory.

Orally or parenterally administrable pharmaceutical compositions in unit dosage form comprise from about 100 to 500 mg of one of the compound of formula (1).

14 Claims, No Drawings

1-ALKYL-3-(ACYLAMINO)-ε-CAPROLACTAMES AS ENHANCERS OF LEARNING AND MEMORY AND PHARMACEUTICAL COMPOSITIONS CONTAINING SAME

The present invention relates to 1-alkyl-3-(acylamino)-ε-caprolactames of formula (1)

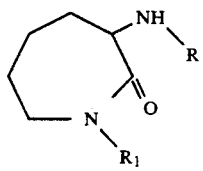

(1)

wherein
R is selected from the group consisting of:
pyrrolidin-2-one-1-acetyl,
p-methoxybenzoyl,
N-benzyloxycarbonyl-(S)-prolyl,
phenylbutanoyl,
3-trifluoromethylbenzoyl,
3,4,5-trimethoxybenzoyl,
nicotinoyl, and
acyl having from 1 to 5 carbon atoms, and
$R_1$ is selected from the group consisting of:
hydrogen,
methoxycarbonylmethyl,
aminocarbonylmethyl,
2-hydroxyethyl, and
formylmethyl,
(provided that, if $R_1$ is hydrogen, R is not formyl or acetyl).

The compounds (1) are potent enhancers of learning and memory.

Because of the presence of a chiral carbon atom, the compounds (1) can exist as two enantiomorphs designated (R) and (S); although both stereoisomers are pharmacologically active, hereinbelow reference shall be made, for the sake of simplicity, to (S)-type structures.

The present invention also relates to orally or parenterally administrable pharmaceutical compositions for enhancing learning and memory, comprising a novel compound of formula (1) as active ingredient.

The known compounds that from the structural and pharmacological viewpoint are the closest ones to the compounds of general formula (1) are piracetam (see e.g. Curr. Dev. Psycopharmacol. 3, 22, 1976) and oxiracetam (see. e.g. II Farmaco. Ed. Sc. 39/1, 16, 1984). As illustrated hereinbelow, the compounds of the present invention are more potent than the known compounds.

The compounds of formula (1) are prepared via a process illustrated in the following synthesis scheme.

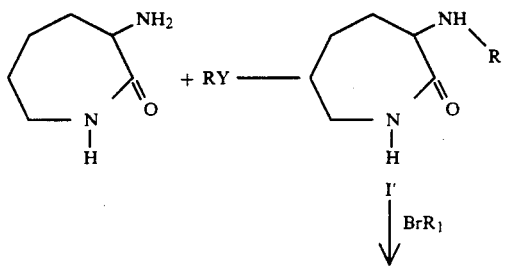

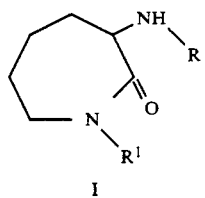

I 3-amino-ε-caprolactam is reacted in an anhydrous, inert organic solvent, such as acetonitrile or methylene chloride or in acetonitrile-$H_2O$ mixture, at room temperature, for 10–24 hours, in equimolar amount with respect to an activated carboxylic acid (Y=COX wherein X represents an activating group) via a halogenating agent, such as thionyl chloride or oxalyl chloride, or a condensating agent, such as dicyclohexylcarbodiimide (DCC), carbonyldiimidazole (CDI), or 2-ethoxy-1-ethoxy-carbonyl-1,2-dihydroquinoline (EEDQ).

The condensation product thus obtained is purified by crystallization or by silica gel chromatography. When $R_1$ is other than hydrogen, the compound of formula 1' is reacted with a halogen derivative (molar ratio 1:2) in an inert solvent, such as acetonitrile or tetrahydrofurane, in the presence of sodium or potassium hydride (molar ratios from 1:1 to 1:2) at room temperature or at the reflux temperature, from 2 to 24 hours, thus giving the compound (1).

The following non-limiting examples illustrate the preparation of some of the compounds of formula (1).

EXAMPLE 1

Preparation of (S)-3-(4-phenylbutanoylamino)-ε-caprolactam (ST 707)

CDI (3,891 g; 24 mmoles) was added to 4-phenylbutyric acid (3.284 g; 20 mmoles) in $CH_2Cl_2$ (100 mL) and the resulting solution was kept under stirring for 30 minutes at room temperature. (S)-3-amino-ε-caprolactam (2.563 g; 20 mmoles) was added and the resulting solution was kept under stirring for 24 hours at room temperature. The organic phase was washed with 1N NaOH (3×30 mL), 1N HCl (3×30 mL), $H_2O$ and NaCl saturated solution, and dried over anhydrous $Na_2SO_4$.

The solvent was evaporated and 5 g of product were obtained.
Yield=90%
M.P.=106°–108° C.
$[\alpha]_D^{25}=+10.2°$ MeOH (C=1)
TLC on silica gel, eluant EtOAc: $R_F=0.28$
Elementary analysis for $C_{16}H_{22}N_2O_2$: Calculated: C,70.04; H,8.08; N 10.21. Found: C,69.94; H,8.43; N 10.16.

$^1$H NMR (CDCl$_3$): δ7.3–7.15(m,5H, aromatic), 6.9(br d,1H, —CHNHCO—), 6.55(br t,1H, —CH$_2$NHCO—), 4.5(m,1H, —CHNCO—), 3.35–3.15(m,2H, —CH$_2$NCO), 2.62(t,2H, —CH$_2$Ph), 2.22(t,2H, —NCOCH$_2$CH$_2$—), 2.1–1.66(m,6H, —CH$_2$CH$_2$CH$_2$CHNCOCH$_2$CH$_2$—), 1.55–1.28(m,2H, —CH$_2$CH$_2$CH$_2$CHNCO—)

HPLC
μBondapack 18: Length=300 mm, Inner Diameter=3.9 mm; Size=10 μm.
Eluant CH$_3$CN/KH$_2$PO$_4$: 0.05M (30:70)
Flow rate=1 mL/min.
Retention time=11.03 min.

EXAMPLE 2

Preparation of
(S)-1-(methoxycarbonylmethyl)-3-(4-phenyl-butanoylamino)-ε-caprolactam (ST 740)

To a solution of ST 707 (prepared as shown in Example 1) (1.5 g; 5.46 mmoles) and $BrCH_2COOCH_3$ (1.672 g; 10.92 mmoles) in $CH_3CN$ (80 mL), 80% NaH in mineral oil (37.82 mg; 10.92 mmoles) was added in two aliquots over one hour. The resulting mixture was kept under stirring at room temperature for 24 hours and then filtered. The filtrate, brought to dryness, was chromatographed on silica gel using EtOAc as eluant. 1.4 g of an oily product were obtained.

Yield = 74%
$[\alpha]_D^{25} = -9.7°$ MeOH (C = 1)
TLC = silica gel; Eluant EtOAc; $R_F = 0.55$
Elementary analysis for $C_{19}H_{26}N_2O_4$; Calculated: C,65.87; H,7.56; N,8.08. Found: C,65.2; H,7.89; N,8.40.
$^1$HNMR ($CDCl_3$): δ7.3–7.15(m,5H, aromatic), 6.9(br d,1H, —CH$\underline{N}$HCO—), 4.72–4.62(m,1H, —C$\underline{H}$NCO—), 4.18(s,2H, —$\underline{N}$CH$_2$CO—), 3.78–3.65(m,4H, —OCH$_3$, —CH$\underline{H}$NCO—), 3.25–3.15(m,1H, —C$\underline{H}$HNCO—), 2.65(t,2H, —C$\underline{H_2}$Ph), 2.2(t,2H, —NCOC$\underline{H_2}$CH$_2$—), 2.1–1.75(m,6H, —CH$_2$CH$_2$CH$_2$CHNCOC$\underline{H_2}$CH$_2$—), 1.7–1.45(m,2H, —C$\underline{H_2}$CH$_2$C$\underline{H_2}$CHN—)
HPLC
LiCHROSORB-RP8: Length = 250 mm; Inner Diameter = 4 mm; size = 5 µm.
Eluant = $CH_3CN/KH_2PO_4$: 0.025M (40:60)
Flow rate = 1 mL/min.
Retention time = 4.18 min.

EXAMPLE 3

Preparation of
(S)-1-(aminocarbonylmethyl)-3-(4-phenyl-butanoylamino)-ε-caprolactam (ST 741)

Gaseous $NH_3$ was bubbled for 30 minutes into a solution of ST 740 (1.6 g; 4.62 mmoles) in MeOH (50 mL) cooled with an ice bath. The solution was kept under stirring at room temperature for 24 hours, the solvent was evaporated and the residue chromatographed on silica gel using EtOAc-MeOH (9:1) as eluant. 1.3 g of product were obtained.

Yield = 85%
M.P. = 153°–155° C.
$[\alpha]_D^{25} = +8.2°$ MeOH (C = 0.5)
TLC on silica gel; eluant EtOAc-MeOH (9:1): $R_F = 0.3$
Elementary analysis for $C_{18}H_{25}N_3O_3$: Calculated: C,65.23; H,7.60; N,12.68. Found: C,64.81; H,7.79; N,12.34.
$^1$HNMR ($CDCl_3$): δ7.31–7.13(m,5H, aromatic), 6.87(br d,1H, —CH$\underline{N}$HCO—), 6.42(br s, —CON$\underline{H}$H), 5.89(br s,1H, —CONH$\underline{H}$), 4.76–4.66(m,1H, —C$\underline{H}$NCO—), 4.29(d,1H, —NC$\underline{H}$HCON—), 3.82(d,1H, —NCH$\underline{H}$CON—), 3.76–3.64(m,1H, CH$_2$C$\underline{H}$HNCO—), 3.35–3.24(m,1H, —CH$_2$C$\underline{H}$HNCO—), 2.63(t,2H, —C$\underline{H_2}$Ph), 2.2(t,2H, —NCOC$\underline{H_2}$CH$_2$—), 2.08–1.74(m,6H, —CH$_2$CH$_2$CH$_2$CHNCOC$\underline{H_2}$CH$_2$—), 1.58–1.38(m,2H, —C$\underline{H_2}$CH$_2$C$\underline{H}$N—)
HPLC
LiCROSORB-RP8: Length = 250 mm; Inner Diameter = 4 mm; size = 5 µm.
Eluant = $CH_3CN/H_2O$ (30:70)
Flow rate = 1 mL/min.
Retention time = 5.00 min

EXAMPLE 4

Preparation of
(S)-1-(2-hydroxyethyl)-3-(4-phenylbutanoylamino)-ε-caprolactam (ST 747)

$NaBH_4$ (402 mg; 10.7 mmoles) was added to ST 740 (1 g; 2.88 mmoles) in tert-butyl alcohol (18 mL), the temperature was brought to 80° C. and MeOH (3 mL) was slowly added. The resulting mixture was kept at the reflux temperature for 2 hours and then cooled to room temperature. Following cooling with an ice bath, $H_2O$ was added and the alcohols were evaporated under vacuum, the aqueous phase was extracted with EtOAc and the solvent was evaporated. The residue was chromatographed on silica gel using EtOAc-MeOH (9:1) as eluant. 530 mg of an oily product were obtained.

Yield = 57%
$[\alpha]_D^{25} = -1°$ MeOH (C = 2.2)
TLC on silica gel; eluant EtOAc-MeOH (9:1): $R_F = 0.4$
Elementary analysis for $C_{18}H_{26}N_2O_3$: Calculated: C,67.89; H,8.23; N,8.79. Found: C,67.40; H,8.34; N,8.34.
$^1$HNMR ($CDCl_3$): δ7.32–7.14(m,5H, aromatic), 6.82(br d,1H, —CHNHCO—), 4.7–4.6(m,1H, —CHNHCO—), 3.82–3.48(m,5H —CHHNCH$_2$C$\underline{H_2}$OH), 3.38–3.26(m,1H, —CH$\underline{H}$NCH$_2$OH), 2.8(br s,1H, —O$\underline{H}$), 2.64(t,2H, —C$\underline{H_2}$Ph) 2.23(t,2H, —NCOCH$_2$C$\underline{H_2}$—), 2.08–1.76(m,6H, —CH$_2$CH$_2$CH$_2$CHNCOC$\underline{H_2}$CH$_2$—), 1.54–1.36(m,2H, —C$\underline{H_2}$CH$_2$C$\underline{H}$N—)
HPLC
µBondapack $C_{18}$: Length = 300 mm; Inner Diameter = 3.9 mm; size = 10 µm.
Eluant = $KH_2PO_4$: 0.05 M/$CH_3CN$ (70:30)
Flow rate = 1 mL/min.
Retention time = 11.62 min.

EXAMPLE 5

Preparation of
(S)-1-(formylmethyl)-3-(phenylbutanoylamino)-ε-caprolactam (ST 800)

To a suspension of KH (35% in mineral oil, 3.726 g 32 mmoles) (washed with pentane) in THF (90 mL) a solution of ST 707 (6 g, 21 mmoles) in THF (90 mL) was added dropwise. The resulting mixture was kept at the reflux temperature until the hydrogen development was over.

Bromoacetaldehyde dimethyl acetal (7.38 g; 43 mmoles) was added dropwise and the resulting mixture was kept at the reflux temperature overnight.

The mixture was evaporated under vacuum, a $NH_4Cl$ saturated solution (200 mL) was added thereto, the resulting mixture was extracted with $CH_2Cl_2$ (3×70 mL) and the organic phase was dried over anhydrous $Na_2SO_4$.

The residue obtained following solvent evaporation was chromatographed on silica gel using EtOAc-Hexane (95:5) as eluant. 4 g of (S)-1-(2,2-dimethoxyethyl)-3-(phenylbutanoylamino)-ε-caprolactam were obtained (TLC silica gel, EtOAc, $R_F = 0.5$) which were dissolved in $CH_3CN$ (100 mL) and $H_2O$ (100 mL). Trifluoroacetic acid (2 mL) was added and the solution was kept under stirring at room temperature overnight. $CH_3CN$ was evaporated under vacuum and the residue extracted with $CHCl_3$(3×50 mL). The organic phase was washed with a NaCl solution, dehydrated over $Na_2SO_4$ and evaporated. 2.3 g of the product were obtained.

Yield = 67%
[α]$_D^{25}$ = +0.9° CHCl$_3$ (C = 1)
TLC on silica gel; eluant EtOAC: R$_F$ = 0.31
Elementary analysis for C$_{18}$H$_{24}$N$_2$O$_3$: Calculated: C,68.33; H,7.64; N,8.85. Found: C,68.37; H,7.59; N,8.66.
$^1$HNMR (CDCl$_3$): δ9.55(s,1H, —HO), 7.30–7.15(m,5-H,aromatic), 6.90(br d,1H, —NHCO—), 4.75–4.65(m,1H, —CHNHCO—), 4.25(dd,2H, —NCH$_2$CHO), 3.80–3.65(m,1H, —CHHNCO—), 3.15–3.05(m,1H, —CHHNCO—) —2.62(t,2H, —CH$_2$Ph), 2.22(t,2H —NCOCH$_2$CH$_2$—), 2.10–1.75(m,6H, —CH$_2$CH$_2$CH$_2$CHNCOCH$_2$CH$_2$), 1.65–1.45(m,2H, —CH$_2$CH$_2$CHNCO—)

EXAMPLE 6

Preparation of (S)-3-[(pyrrolidin-2-one-1-yl)acetylamino]-ε-caprolactam (ST 721)

To (pyrrolidin-2-one-1-yl)acetic acid (1.43 g: 10 mmoles) in CH$_2$Cl$_2$ (50 mL), CDI (1.96 g; 12 mmoles) was added under stirring and after 30 minutes (S)-3-amino-ε-caprolactam (1.28 g; 10 mmoles) was added. The reaction mixture was kept under stirring at room temperature for 24 hours. To the resulting mixture Et$_2$O was added under stirring and by filtration under vacuum 2 g of product were obtained which was further purified by crystallization from CH$_3$CN furnishing 1.3 g of product (yield on the crystallized product 50%).
M.P. = 245°–247° C.
[α]$_D^{25}$ = +7.1° MeOH (C=1)
TLC on silica gel; eluant EtOAc-MeOH (7:3): R$_F$ = 0.43
Elementary analysis for C$_{12}$H$_{19}$N$_3$O$_3$: Calculated: C,56.9; H,7.5; N,16.5. Found: C,57.07; H,7.95; N,16.94.
$^1$HNMR (D$_2$O): δ4.65(m,1H, —CHNHCO), 4.05(s,2H, —COCH$_2$NCH$_2$—), 3.5(t,2H, —COCH$_2$NCH$_2$—), 3.4–3.2(m,2H, CH$_2$NHCO—), 2.5(t,2H, —CH$_2$NCOCH$_2$—), 2.20–1.60(m,6H, —CH$_2$CH$_2$CH$_2$CHN—, —CH$_2$CH$_2$CON—), 1.45–1.30(m,2H, —CH$_2$CH$_2$CHN—).
HPLC
Partisil 10 scx: Length = 250 mm; Inner Diameter = 4.6 mm
Eluant = CH$_3$CN/KH$_2$PO$_4$: 0.05M (65:35)
Flow rate = 1 mL/min.
Retention time = 4.15 min.

EXAMPLE 7

Preparation of (S)-3-(benzyloxycarbonyl)-(S)-prolylamino)-ε-caprolactam (ST 725)

EEDQ (3.45 g; 13.95 mmoles) was added under stirring to (S)-benzyloxycarbonyl prolin (2.9 g; 11.63 mmoles) in CH$_3$CN (100 mL) and after 30 minutes (S)-3-amino-ε-caprolactam was added (1.49 g; 11.63 mmoles).
The reaction mixture was kept a room temperature for 24 hours; the solvent was evaporated under vacuum and the residue chromatographed on silica gel using EtOAc as eluant, 2.9 g of product were obtained.
Yield = 70%
M.P. = 156°–158° C.
[α]$_D^{25}$ = −69.7° MeOH (C=1)
TLC on silica gel; eluant EtOAc: R$_F$ = 0.23
Elementary analysis for C$_{19}$H$_{25}$N$_3$O$_4$: Calculated: C,63.49; H,7.01; N,11.69. Found: C,63.13; H,7.25; N,12.10.

$^1$HNMR(CDCl$_3$): δ7.5–7.2(m,6H,aromatic, —CH$_2$NHCO—), 6.65(br, 1H, —CHNHCO—), 5.25–5.05(m,2H, —OCH$_2$Ph), 4.55–4.20(m,2H, —N-COCHNCO—, —CHNCOO—) 3.7–3.42(m,2H, —CH$_2$-NCOO—), 3.35–2.15(m,2H, —CH$_2$NHCO—), 2.25–1.7(m,8H, —CH$_2$CH$_2$CH$_2$CH—, —CH$_2$CH$_2$C-HN—), 1.6–1.2(m,2H, —CH$_2$CH$_2$CH$_2$CH$_2$CH—).
HPLC
μBondapack C$_{18}$: Length = 300 mm; Inner Diameter = 3.9 mm; size = 10 μm.
Eluant = KH$_2$PO$_4$: 0.05 M/CH$_3$CN (80:20)
Flow rate = 1.5 mL/min.
Retention time = 19.46 min.

EXAMPLE 8

Preparation of (S)-3-(4-methoxybenzoylamino)-ε-caprolactam (ST 734)

CDI (1.96 g; 12 mmoles) was added under stirring to 4-methoxybenzoic acid (1.52 g; 10 mmoles) in CH$_2$Cl$_2$ (50 mL) and after 30 minutes (S)-3-amino-ε-caprolactam (1.28 g, 10 mmoles) was added. The reaction mixture was kept under stirring at room temperature for 24 hours, the solvent was evaporated and the residue chromatographed on silica gel using EtOAc-MeOH as eluant (9:1).
The solid thus obtained was taken up with CH$_2$Cl$_2$ e precipitated with Et$_2$O obtaining 1.3 g of product.
Yield = 50%
M.P. = 170°–172° C.
[α]$_D^{25}$ = +42.2° MeOH (C=1)
TLC on silica gel; eluant EtOAc: R$_F$ = 0.3
Elementary analysis for C$_{14}$H$_{18}$N$_2$O$_3$: Calculated: C,64.10; H,6.91; N,10.68. Found: C,64.51; H,6.99; N,10.50.
$^1$HNMR(CDCl$_3$): δ7.82(d,2H,aromatic), 7.58(br d,1H, —CHNHCO—), 6.93(d,2H,aromatic), 6.58(br t, 1H, —CH$_2$NHCO—), 4.76–4.66(m,1H, —CHNCO—), 3.85(s,3H —OCH$_3$), 3.42–3.22(m,2H, CH$_2$NCO—), 2.3–2.18(m,1H, —CHHCHN—), 2.1–1.82(m,3H, —CH$_2$CH$_2$CHHCHN—), 1.64–1.35(m,2H, —CH$_2$CH$_2$CHNCO—).
HPLC
μBondapack C$_{18}$: Length = 300 mm; Inner Diameter = 3.9 mm; Size = 10 μm.
Eluant = KH$_2$PO$_4$: 0.05/CH$_3$CN (60:40)
Flow rate = 1 mL/min.
Retention time = 4.9 min.

EXAMPLE 9

Preparation of (S)-3-(3-trifluoromethylbenzoylamino)-ε-caprolactam (ST 796)

CDI (2.81 g, 17.36 mmoles) was added to trifluoromethylbenzoic acid (3 g, 15.78 mmoles) in CH$_2$Cl$_2$ (60 mL). The solution was kept under stirring for 30 minutes at room temperature and (S)-3-amino-ε-caprolactam (2.02 g, 15.78 mmoles) was added. After 24 hours the resulting mixture was taken up with CHCl$_3$ (50 mL), the organic phase was washed with HCl 1N (3×30 mL). NaOH 1N (3×30 mL), H$_2$O, NaCl saturated solution and then dried over anhydrous Na$_2$SO$_4$. The residue obtained by evaporation of the solvent was chromatographed on silica gel using EtOAc-MeOH as eluant (ratio 8:2) yielding 3.5 g of product.
Yield = 74%
M.P. = 218°–219° C.

$[\alpha]_D^{25} = +26.9°$ MeOH (C=1)

TLC on silica gel; eluant EtOAc-MeOH 95:5; $R_F=0.5$

Elementary analysis for $C_{14}H_{15}F_3N_2O_2$: Calculated: C,55.99; H,5.03; N,9.33. Found: C,56.09; H,5.03; N,9.53.

$^1$HNMR(CDCl$_3$/DMSO-d$_6$): δ8.15(s,1H,aromatic), 8.05(d,1H,aromatic), 7.9(br,1H, —HNCOPh), 7.78(d,1H,aromatic), 7.6(m,1H,aromatic), 7.6(m,1H,aromatic), 7.35(br,1H, —CH$_2$NHCO—), 4.75-4.65(m,1H, —CHNCO—), 3.40-3.22(m,2H, —CH$_2$NCO—), 2.25-2.15(m,1H, —CHHCHN—), 2.12-2.02(m,1H, —CHHCHN—), 1.98-1.8(m,2H, CH$_2$CH$_2$CH$_2$CHN—), 1.67-1.35(m,2H, —CH$_2$CH$_2$C-HN—)

HPLC

Lichrosorb RP-18: Length=250 mm; Inner Diameter=4 mm; size=10 µm.

Eluant=KH$_2$PO$_4$: 0.05 M/CH$_3$CN (80:20)

Flow rate=1 mL/min.

Retention time=18.59 min.

EXAMPLE 10

Preparation of (S)-3-(3,4,5-trimethoxybenzoylamino)-ε-caprolactam (ST 819)

CDI (3.96 g, 24.44 mmoles) was added to 3,4,5,-trimethoxybenzoic acid (4 g, 18.8 mmoles) in CH$_2$Cl$_2$ (60 mL). The solution was kept under stirring for 30 minutes at room temperature and (S)-3-amino-ε-caprolactam (2.41 g, 18.8 mmoles) was added. After 24 hours the resulting mixture was taken up with CHCl$_3$ (50 mL), the organic phase was washed with HCl 1N (3×30 mL), NaOH 1N (3×30 mL), H$_2$O, NaCl saturated solution and dried on anhydrous Na$_2$SO$_4$. The evaporation residue was chromatographed on silica gel using EtOAc-MeOH as eluant, (ratio 95:5) giving thus 3.1 g of product.

Yield=51%

M.P.=95°-97° C.

$[\alpha]_D^{25}=+35.7°$ MeOH (C=0.9)

TLC on silica gel; eluant EtOAC-MeOH 95:5; $R_F=0.28$

Elementary analysis for $C_{16}H_{22}N_2O_5$: Calculated: C,59.61; H,6.88; N,8.69. Found: C,59.10; H,7.17; N,8.48.

$^1$HNMR(CDCl$_3$): δ7.65(br,1H, —HNCOPh—), 7.10(s,2H,aromatic), 6.75(br,1H, —CH$_2$NHCO—), 4.78-4.68(m,1H, —CHNCO—), 3.94(s,6H,2m-OCH$_3$), 3.88(s,3H,p-OCH$_3$), 3.42-3.22(m,2H, —CH$_2$NHCO—), 2.28-2.19(m,1H, —CHHCHN—), 2.12-2.02(m,1H, —CHHCHN—), 2.0-1.82(m,2H, —CH$_2$CH$_2$CH$_2$CHN—), 1.65-1.35(m,2H, —CH$_2$CH$_2$CHN—).

HPLC

Lichrosorb RP-18: Length=250 mm; Inner Diameter=4 mm; size=10 µm.

Eluant=KH$_2$PO$_4$ 0.05 M/CH$_3$CN (70:30)

Flow rate=1 mL/min.

Retention time=5.96 min.

EXAMPLE 11

Preparation of (S)-3-(nicotinoylamino)-ε-caprolactam (ST 807)

EEDQ (7.52 g, 30.4 mmoles), (S)-3-amino-ε-caprolactam (3 g, 23.4 mmoles), and H$_2$O were added to nicotinic acid (2.28 g, 23.4 mmoles) in CH$_3$CN until complete solubilization. After stirring overnight at room temperature the solvents were evaporated, the residue was taken up with CHCl$_3$ and Et$_2$O was added under stirring until complete precipitation. The solid residue obtained by filtration (3.5 g) was further purified by chromatography on silica gel using EtOAc-MeOH as eluant (8:2). 3.15 g of product were obtained.

Yield=57%

M.P.=177° C.

$[\alpha]_D^{25}=+88°$ CHCl$_3$ (C=1)

TLC on silica gel; eluant EtOAc-MeOH 8:2: $R_F=0.38$

Elementary analysis for $C_{12}H_{15}N_3O_2$: Calculated: C,61.79; H,6.48; N,18.01. Found: C,61.36; H,6.49; N,17.95.

$^1$HNMR(CDCl$_3$): δ9.08(m,1H,aromatic), 8.75(m,1H,aromatic), 8.15(m,1H, aromatic), 7.75(br,1H, —CHNHCO—), 7.40(m,1H,aromatic), 6.40(br,1H, —CH$_2$NHCO—), 4.76-4.68(m,1H, —CHNCO—), 3.42-3.22(m,2H, —CH$_2$NCO—), 2.30-2.21(m,1H, —CHHCHN—), 2.13-2.01(m, —CHHCHN—), 2.0-1.78(m,2H, —CH$_2$CH$_2$CH$_2$CHN—), 1.65-1.38(m,1H, —CH$_2$CH$_2$CHN—).

HPLC

µBondapack NH2; Length=300 mm; Inner Diameter=3.9 mm; Size=10 µm.

Eluant=CH$_3$CN/KH$_2$PO$_4$: 0.05M (65:35)

Flow rate=1 mL/min.

Retention time=3.3 min.

EXAMPLE 12

Preparation of (S)-1-(methoxycarbonylmethyl)-3-formylamino-ε-caprolactam (ST 919)

The title compound was prepared as described in Example 2, using (S)-3-formylamino-3-ε-caprolactam as starting compound.

Yield=70%

M.P.=60°-62° C.

$[\alpha]_D^{25}=+1.2°$ MeOH (C=1)

TLC on silica gel; eluant EtOAc: $R_F=0.24$

Elementary analysis for $C_{10}H_{16}N_2O_4$ Calculated: C, 52.62; H, 7.06; N, 12.27. Found: C, 52.25; H, 7.05; N, 11.92.

$^1$HNMR(CDCl$_3$): δ8.15(s,1H, —NCHO), 7.10(br s,1H, —NHCHO), 4.78-4.68(m,1H, —CHNCO—), 4.18(s,2H, —NCH$_2$CO—), 3.78-3.62(m,4H, —OCH$_3$, —CH$_2$CHHNCO—), 3.25-3.15(m,1H, —CH$_2$CHH-NCO—), 2.15-1.48(m,6H, —CH$_2$CH$_2$CH$_2$CHN—)

HPLC

µ Bondapack-C18: Length=300 mm; Inner Diameter=3.9 mm; Size=10 µm.

Eluant=KHPO$_4$ 0.05M/CH$_3$CN (80:20)

Flow rate=1 mL/min.

Retention time=5.51 min.

EXAMPLE 13

Preparation of (S)-1-(aminocarbonylmethyl)-3-formylamino-ε-caprolactam (ST 893)

The title compound was prepared as described in Example 3 by substituting ST 919 (see Example 12) for ST 740 as starting compound.

As chromatography eluant, EtOAc-MeOH (7:3) was used.

Yield=80%

M.P.=208°-210° C.

$[\alpha]_D^{25}=+12.4°$ MeOH(C=0.5)

TLC on silica gel; eluant EtOAc MeOH 7:3: $R_F=0.46$

Elementary analysis $C_{19}H_{15}N_3O_3$: Calculated: C, 50.65; H, 7.09; N, 19.70. Found: C, 50.32; H, 6.85; N, 19.29.

$^1$HNMR(D$_2$O): δ8.08(s,1H, —NCHO), 4.9(m,1H, —CHNCO), 4.39(d,J=16.6 Hz,1H, —NCHHCON—), 3.98(d,J=16.6 Hz,1H, —NCHHCON), 3.85–3.75(m,1H, —CH$_2$CHHNCO—), 3.42–3.3(m,1H, —CH$_2$CHHNCO—), 2.05–1.48(m,6H, —CH$_2$CH$_2$CH$_2$CHN—)

HPLC

μ Bondapack-NH$_2$: Length=300 mm; Inner Diameter=3.9 mm; Size=10 μm.

Eluant=CH$_3$CN/KH$_2$PO$_4$: 0.05M PH=6.5; con-KOH

Flow rate=1 mL/min.

Retention time=3.95 min.

EXAMPLE 14

Preparation of (S)-1-(2-hydroxyethyl)-3-formylamino-ε-caprolactam (ST 920)

The title compound was prepared as described in Example 4 by substituting ST 919 (see Example 12) for ST 740.

Water was added to the reaction mixture, the alcohols were evaporated under vacuum, the aqueous phase was washed with EtOAc and evaporated to dryness under vacuum. The residue was chromatographed on silica gel using EtOAC-MeOH (95:5) as eluant.

Yield=55%

M.P.=89°–92° C.

$[\alpha]_D^{25}=+6.5°$ MeOH(C=0.5)

TLC on silica gel: eluant EtOAc-MeOH 9:1; $R_F=0.33$

Elementary analysis for $C_9H_{16}N_2O_3$: Calculated: C, 53.98; H, 8.05; N, 13.99. Found: C, 53.64; H, 7.88; N, 13.58.

$^1$HNMR(CDCl$_3$): δ8.1(s,1H, —NCHO), 7.1(br s,1H, —NHCHO—), 4.8–4.65(m,1H, —CHNCO—), 3.9–3.45(m,5H, —CHHNCH$_2$CH$_2$OH), 3.4–3.26(m,1H, —CHHNCH$_2$CH$_2$OH), 2.85(br s,1H, OH), 2.14–1.76(m,4H, —CH$_2$CH$_2$CH$_2$CHN—), 1.58–1.36(m,2H, —CH$_2$CH$_2$CH$_2$CHN—)

HPLC

μ Bondapack-NH$_2$: Length=300 mm; Inner Diameter=3.9 mm; Size=10 μm.

Eluant=CH$_3$CN/KH$_2$PO$_4$: 0.05M (65:35)

Flow rate=1 mL/min.

Retention time=3.57 min.

EXAMPLE 15

Preparation of (R)-3-(3-trifluoromethylbenzoylamino)-ε-caprolactam (ST 837)

The title compound was prepared as described in Example 9 by substituting (R)-3-amino-ε-caprolactam for (S)-3-amino-ε-caprolactam as starting compound.

$[\alpha]_D^{25}=-26.3°$ MeOH (C=1)

Other physico-chemical characteristics identical to those of ST 796 (see example 9).

The activity of the compounds of the invention was assessed in several pharmacological tests. Some of these tests wherein piracetam was used as reference standard are illustrated hereinbelow.

(A) Assessment of the Antiamnesic Activity

In order to assess the antiamnesic activity the passive avoidance test in mice was used. Amnesia was brought about by administration of scopolamine (cfr. Bammer, Pharmacological investigations of neurotransmitter involvement in passive avoidance responding: a review and some new results. Neurosci. Biobehav. Rev., 6 (3) 247–296, 1982); or by electroconvulsive shock (ECS) (cfr. Bammer et al., A screening method for substances potentially active on learning and memory. J. Pharmacol. Methods Vol.: 8 (4) 255–263, 1982).

Male CDI mice (Charles River—Italy) weighing 25–26 g were used for the scopolamine-induced amnesia test.

Male CDI mice (Charles River—Germany) fed on a normal diet, were used for the ECS-induced amnesia test.

The compounds were administered i.p.; 0.9 mg/kg in the scopolamine-induced amnesia test; and 9 and 0.9 mg/kg in the ECS-induced amnesia test. All doses were equimolar to piracetam.

The compounds were dissolved in saline.

The apparatus for passive avoidance conditioning was a black plastic chamber (42×42 cm, height 40 cm) provided with a floor constructed of metal rods that could be electrified. From the front wall extended a white runway, 30 cm long and 10 cm wide provided with side walls 12 cm high, which led into the box through a guillotine door. The runway was lightened by a 60 W lamp (cfr. Ader et al., Retention of passive avoidance response as a function of the intensity and duration of electric shock. Psychon. Sci., 26 (3), 125–127, 1972).

Passive Avoidance Following Scopolamine-Induced Amnesia

The animals were administered the compounds and scopolamine (1.5 mg/kg s.c.) 30 minutes and 15 minutes, respectively, before the test and were then placed on the runway. After one minute of adaptation, the door was raised and the time employed by the animal to enter the darkened box with all four feet, was recorded.

Upon entry, the guillotine door was lowered and three seconds thereafter the rods were electrified, 0.21 mA for 2 seconds.

Immediately thereafter the animal was placed in the housing cage. Retention was assessed 24 hours later by placing the animal on the runway and again evaluating the latency in entering the chamber, using an end-point of 300 s (cfr. Bammer, loc. cit.).

In each experiment, two groups of animals in addition to the treated ones were used, that were defined as follows:

(1) ceiling control animals (treated with placebo and not subjected to amnesia treatment with scopolamine or ECS) to ensure that these animals not treated with the amnesia agent remembered the task;

(2) base-line control animals (treated with placebo and subjected to amnesia treatment with scopolamine or ECS) to ensure that ECS or scopolamine produced amnesia in the animals not treated with the compounds of the present invention.

The results of each compound under examination were expressed as percentage of amnesia reversal (AR) in order to make comparisons across the tested compounds.

AR is defined as follows:

$$AR = \frac{CI_t}{CI_c} \cdot 100$$

wherein CI, comparison index (the subscripts "t" and "c" refer to "treated" and "ceiling control", respectively) is defined by the formula $$CI = [\Sigma A_{ij}/N_i \cdot N_j] \, 100$$

wherein
- $N_i$ is the number of animals belonging to the i-nth group (ceiling control or treated animals);
- $N_j$ is the number of animals belonging to the j-nth group (base-line control animals), and
- $A_{ij}$ is a binary function that can take only the values $+1$, $0$ or $-1$ depending on whether the latency time (in seconds) of an animal belonging to the i-nth group, $X_i$, is higher than, the same as or smaller than the latency time (in seconds) of an animal of the j-nth group, $X_j$.

The sum $\Sigma A_{ij}$ encompasses all the possible pairs obtained by combining each term $X_i$ with each term $X_j$.

Whenever in performing the test the comparison index (CI) between ceiling control animals and base-line control animals, generally expected to range between 60 and 80%, turned out to be lower than 40%, the data for the whole experiment were discarded.

The results are shown in Table 1. In particular, at the dose of 0.9 mg/kg, the amnesia reversal of ST 796 and ST 800 was 65% and 64%, respectively. ST 734 and ST 893 showed to be inactive. ARs of Piracetam, ST 725 and ST 837 were 19%, 29% and 15%, respectively.

TABLE 1

Passive avoidance following scopolamine-induced amnesia. The Table shows the ARs of some compounds of the present invention. The number of animals (n.) and the AR of each compound are reported.

|  | 0.9 mg kg$^{-1}$ | |
|---|---|---|
|  | n° | % AR |
| Animals in the ceiling control group | 368 | 100 |
| Animals in the base-line control group | 648 | 0 |
| PIRACETAM | 10 | 19 |
| ST 725 | 32 | 29 |
| ST 734 | 12 | 0 |
| ST 796 | 36 | 65 |
| ST 800 | 12 | 64 |
| ST 837 | 48 | 15 |
| ST 893 | 10 | 0 |

Passive Avoidance Following ECS-Induced Amnesia 30 minutes following treatment with the compounds, the animals were placed on the runway. After one minute of adaptation, the door was raised and the time employed by the animal to enter the darkened box with all four feet, was recorded.

Upon entry, the guillotine door was lowered and three seconds thereafter the rods were electrified, 0.24 mA for 2 seconds.

The mouse was then removed from the chamber and immediately administered an electroshock delivered through spring clips attached to the ears (square wave, intensity 20 mA, amplitude 0.6 msec, duration 0.5 s, frequency 50 Hz).

Retention was assessed 24 hours later by placing the animal on the runway and again evaluating the latency in entering the chamber, using an end-point of 300 seconds (Bammer, loc. cit.). In each experiment, two groups of animals (a ceiling control group and a base-line control group) in addition to the treated animals were used, as previously described.

The results for each compound under examination were expressed as amnesia reversal (AR) in such a way as to make comparisons across the tested compounds. Amnesia reversal was assessed by using the comparison index (CI), calculated according to the formula previously given.

The results obtained are shown in table 2. In particular, at the dose of 9 mg/kg piracetam and ST 837 are inactive, ST 725 and ST 893 exhibit 12% and 9%, respectively, of amnesia reversal; ST 734, ST 796 and ST 800 exhibit 37%, 35% and 38%, respectively, of amnesia reversal.

At the lower dose, i.e. 0.9 mg/kg. ST 734 and ST 796 are still active, exhibiting 37% amnesia reversal; at this dose, besides piracetam, also ST 725 and ST 800 are inactive. Surprisingly, at this dose, ST 893 and ST 837 turned out to be active, exhibiting 55% and 21%, respectively, of amnesia reversal.

TABLE 2

Passive avoidance following ECS-induced amnesia. The table shows the ARs of some compounds of the present invention. The number of animals (n.) and AR of each tested compound at various dose levels are reported.

|  | 9 mg kg$^{-1}$ | | 0.9 mg kg$^{-1}$ | |
|---|---|---|---|---|
|  | n° | AR | n° | AR |
| Ceiling control | 546 | 100 | 538 | 100 |
| Base-line control group | 1030 | 0 | 1047 | 0 |
| PIRACETAM | 30 | 0 | 27 | 0 |
| ST 725 | 12 | 12 | 10 | 0 |
| ST 734 | 24 | 37 | 23 | 37 |
| ST 796 | 12 | 35 | 12 | 37 |
| ST 800 | 12 | 38 | 12 | 0 |
| ST 837 | 12 | 0 | 34 | 21 |
| ST 893 | 12 | 9 | 24 | 55 |

(B) Behavioral Profile

The behavioral profile was assessed in male CDI mice (Charles River, Italy) weighing 22–24 g. using the Irwin test (IRWIN S., Drug screening and evaluation procedures. 136, 123–128, 1962). The animals had been caged under normal conditions and kept fasting for the last 18 hours. Following administration of the compounds, the behaviour of the animals was monitored for 6 hours.

The compounds were suspended in 10% arabic gum and orally administered at doses equimolar to 90, 23, 5.4 and 1.4 mg piracetam/10 mL/kg of body weight.

The animals of the control groups were administered 10% arabic gum (10 mL/kg, orally).

No compound altered, at the tested doses, the behavioural profile.

(C) Analgesic activity

The analgesic activity was assessed in CDI mice (Charles River, Italy) weighing 22-24 g, utilizing the hot plate test (56° C.).

The animals, kept under normal caging conditions and kept fasting for 18 hours, were placed on the hot plate for 30, 60, 120 and 180 minutes following the administration of 90, 23, 5.4 and 1.4 mg/10 mL/kg of each compound under examination.

The analgesic activity was assessed by measuring the increase (in seconds) of the time the animals continued to stay on the hot plate. None of the tested compounds was shown to possess analgesic activity.

The compounds of the present invention can be formulated into orally or parenterally administrable pharmaceutical compositions. Suitable excipient and compositions for tablets, vials and the like are illustrated in the Canadian patent 1,100,515.

Pharmaceutical compositions in unit dosage form comprise between about 100 and about 500 mg of active ingredient.

We claim:

1. 1-alkyl-3-(acylamino)-ε-caprolactames of formula (1)

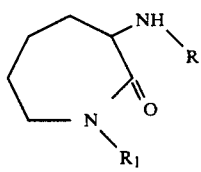

(1)

wherein R selected from the group consisting of: pyrrolidin-2-one-1-acetyl, p-methoxybenzoyl, N-benzoyloxycarbonyl-(S)-prolyl, phenylbutanoyl, -trifluoromethylbenzoyl, 3,4,5-trimethoxybenzoyl, nicotinoyl, and carboxylic acid acyls having from 1 to 5 carbon atoms and wherein $R_1$ is selected from the group consisting of: hydrogen, methoxycarbonylmethyl, aminocarbonylmethyl, 2-hydroxyethyl, and formylmethyl provided that, if $R_1$ is hydrogen, R is not formyl or acetyl.

2. A compound according to claim 1, wherein $R_1$ is hydrogen and R is phenylbutanoyl.

3. A compound according to claim 1, wherein $R_1$ is methoxy carbonylmethyl and R is phenylbutanoyl.

4. A compound according to claim 1, wherein $R_1$ is amino carbonyl methyl and R is phenylbutanoyl.

5. A compound according to claim 1, wherein $R_1$ is hydroxyethyl and R is phenylbutanoyl.

6. A compound according to claim 1, wherein $R_1$ is formylmethyl and R is phenylbutanoyl.

7. A compound according to claim 1, wherein $R_1$ is H and R is pyrrolidin-2-one-1-acetyl.

8. A compound according to claim 1, wherein $R_1$ is H and R is N-benziloxycarbonyl-(S)-prolyl.

9. A compound according to claim 1, wherein $R_1$ is H and R is p-methoxy benzoyl.

10. A compound according to claim 1, wherein $R_1$ is H and R is 3-trifluoromethylbenzoyl.

11. A compound according to claim 1, wherein $R_1$ is H and R is 3,4,5-trimethoxy benzoyl.

12. A compound according to claim 1, wherein $R_1$ is H and R is nicotinyl.

13. An orally or parenterally administrable pharmaceutical composition for enhancing learning and memory which comprises as an active ingredient a 1-alkyl-3-(acylamino)-ε-caprolactames of formula (1)

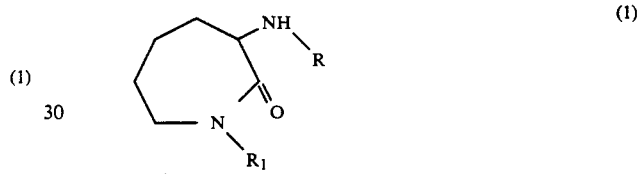

(1)

wherein R selected from the group consisting of: pyrrolidin-2-one-1-acetyl, p-methoxybenzoyl, N-benzoyloxycarbonyl-(S)-prolyl, phenylbutanoyl, 3-trifluoromethylbenzoyl, 3,4,5-trimethoxybenzoyl, nicotinoyl, and carboxylic acid acyls having from 1 to 5 carbon atoms and wherein $R_1$ is selected from the group consisting of: hydrogen, methoxycarbonylmethyl, aminocarbonylmethyl, 2-hydroxyethyl, and formylmethyl provided that, if $R_1$ is hydrogen, R is not formyl or acetyl, and a pharmaceutically acceptable excipient.

14. The pharmaceutical composition according to claim 13 in unit dosage form, which comprises from about 100 to about 500 mg of a compound of formula (1).

* * * * *